(12) United States Patent
Ma et al.

(10) Patent No.: US 11,096,657 B2
(45) Date of Patent: Aug. 24, 2021

(54) LASER LIGHT SOURCE FOR INSTRUMENT TIP VISUALIZATION

(71) Applicant: FUJIFILM SonoSite, Inc., Bothell, WA (US)

(72) Inventors: Qinglin Ma, Kirkland, WA (US); Paul Thurman Dunham, Bothell, WA (US); Keith David Williams, Seattle, WA (US); Hiroshi Murakami, Redmond, WA (US); Wealth Salvador, Seattle, WA (US); Carl Fabian, Beaverton, OR (US); Brian R. Twehues, Seattle, WA (US)

(73) Assignee: FUJIFILM SONOSITE, INC., Bothell, WA (US)

( * ) Notice: Subject to any disclaimer, the term of this patent is extended or adjusted under 35 U.S.C. 154(b) by 493 days.

(21) Appl. No.: 15/612,725

(22) Filed: Jun. 2, 2017

(65) Prior Publication Data

US 2018/0153412 A1 Jun. 7, 2018

Related U.S. Application Data

(60) Provisional application No. 62/430,298, filed on Dec. 5, 2016.

(51) Int. Cl.
*A61B 5/00* (2006.01)
*A61B 8/00* (2006.01)
(Continued)

(52) U.S. Cl.
CPC .......... *A61B 8/0841* (2013.01); *A61B 5/0095* (2013.01); *A61B 5/061* (2013.01);
(Continued)

(58) Field of Classification Search
CPC . A61B 2576/00; A61B 5/0084; A61B 5/0095; A61B 5/06; A61B 5/061;
(Continued)

(56) References Cited

U.S. PATENT DOCUMENTS

| 5,722,852 A | * | 3/1998 | Miek | H01R 12/616 |
| | | | | 439/404 |
| 8,150,325 B1 | * | 4/2012 | Prichard | H04B 1/525 |
| | | | | 324/691 |

(Continued)

FOREIGN PATENT DOCUMENTS

JP 2010005194 A 1/2010

OTHER PUBLICATIONS

JAMECO Electronics (Electromechanical Switches: Choosing the Right Switch), 2010 (Year: 2010).*

(Continued)

*Primary Examiner* — Joanne M Hoffman
*Assistant Examiner* — Alexei Bykhovski
(74) *Attorney, Agent, or Firm* — Womble Bond Dickinson (US) LLP

(57) ABSTRACT

A laser light source transmits laser light to a tip of an interventional instrument such as a needle via an optical fiber. The laser light is absorbed at the distal tip of the instrument and generates a photoacoustic signal. The laser light source is configured to receive a trigger signal from an ultrasound machine when a laser pulse is to be produced. The light source signals the ultrasound machine when an optical connector is connected to the laser light source to automatically begin a needle tip (NTV) visualization mode. If the optical connector is removed from the laser light source, the laser light source stops producing laser light pulses.

20 Claims, 12 Drawing Sheets

(51) Int. Cl.
 *A61B 8/08* (2006.01)
 *A61B 5/06* (2006.01)
 *A61B 8/14* (2006.01)

(52) U.S. Cl.
 CPC .......... *A61B 5/6848* (2013.01); *A61B 8/5207* (2013.01); *A61B 5/0084* (2013.01); *A61B 5/06* (2013.01); *A61B 8/14* (2013.01); *A61B 8/463* (2013.01); *A61B 8/469* (2013.01); *A61B 8/5261* (2013.01); *A61B 2576/00* (2013.01)

(58) Field of Classification Search
 CPC ....... A61B 5/6848; A61B 8/0841; A61B 8/14; A61B 8/463; A61B 8/469; A61B 8/5207; A61B 8/5261
 See application file for complete search history.

(56) References Cited

U.S. PATENT DOCUMENTS

| | | | |
|---|---|---|---|
| 8,232,891 B2* | 7/2012 | Wu | G06F 11/326 340/691.1 |
| 2009/0289200 A1* | 11/2009 | Ishii | A61B 1/00009 250/459.1 |
| 2012/0065469 A1* | 3/2012 | Allyn | A61B 1/005 600/109 |
| 2013/0226002 A1 | 8/2013 | Miyachi | |
| 2014/0378796 A1 | 12/2014 | Chen et al. | |
| 2015/0297092 A1 | 10/2015 | Irisawa | |
| 2016/0061650 A1* | 3/2016 | Sato | A61B 5/0095 73/655 |
| 2016/0287278 A1 | 10/2016 | Stigall et al. | |
| 2017/0079622 A1* | 3/2017 | O'Donnell | A61B 5/0035 |
| 2017/0219555 A1* | 8/2017 | Nazzaro | G01N 33/4875 |
| 2019/0008393 A1* | 1/2019 | Irisawa | A61B 5/0095 |

OTHER PUBLICATIONS

Ertle et al. (The Illuminated Laser Warning Sign, Photonics Spectra, Photonics Media Press, Dec. 2007) (Year: 2007).*
Telenkov, et al. (Photoacoustic correlation signal-to-noise ratio enhancement by coherent averaging and optical waveform optimization, Rev. Sci. Instrum. 84, 104907, pp. 1-7 (2013) (Year: 2013).*
International Searching Authority, International Search Report and Written Opinion, PCT Patent Application PCT/US2017/064666, dated Mar. 29, 2018, 11 pages.
PCT International Preliminary Report on Patentability for PCT/US2017/064666, dated Jun. 11, 2019, 7 pages.

* cited by examiner

LASER LIGHT SOURCE FOR INSTRUMENT TIP VISUALIZATION

RELATED APPLICATION

The present application claims the benefit of, and priority to, U.S. Provisional Application No. 62/430,298 filed Dec. 5, 2016, which is herein incorporated by reference in its entirety.

TECHNICAL FIELD

The following disclosure is generally directed to systems for detecting the location of an interventional instrument in a subject. In particular, one or more aspects of the disclosed technology are directed a laser light source for producing a photoacoustic signal at an end portion of an interventional instrument.

BACKGROUND

Many medical procedures require the accurate placement of an instrument in the body. For example, during a nerve block procedure, a physician and their assistant attempt to place a needle for delivering anesthetic near a particular nerve. Because the tip of the needle is in the body and can bend as it is being advanced, the exact location of the nerve is unknown. Therefore different techniques and tools are available to help the physician determine if the needle tip is in the correct location. For example, nerve stimulators can help confirm the location of a needle tip in the proximity of a nerve by applying a small amount of electricity to the patient's body to stimulate the nearby nerve. If the correct muscle associated with the targeted nerve responds to the electricity, the operator knows that he/she has reached the proximity of the target nerve to be blocked, and can then inject a drug.

Conventional ultrasound needle guidance technology can also be used to determine the nerve and the needle location. One method, for example, involves enhancing and/or modifying ultrasound imaging parameters to emphasize the shaft of a needle that is in the same plane as the ultrasound image. Another method involves the use of an echogenic needle having laser-etched patterns on the needle shaft that enhance specular reflectivity when the needle is placed in the subject at a steep angle. Some predictive methods infer the location of a needle and its tip using magnetic and/or optical sensors attached to an ultrasound transducer and/or a needle. These predictive methods can be cumbersome, however, adding bulk and cost to an ultrasound transducer and typically require substantial training. Furthermore, since the location of the needle tip is inferred, a bent needle can lead to inaccuracies in the predicted needle tip location.

Another approach that is being developed is to use photoacoustics to locate a needle tip. With this method, one or more laser light pulses are transmitted to an optical absorber at the distal tip of an optical fiber that cause the absorber to rapidly heat and expand on a microscopic scale compared to the surrounding tissue. The expansion creates ultrasonic vibrations that can be detected with an ultrasound transducer. While some ultrasound machines are being designed with the capability to interface with a laser source that delivers such laser pulses and to detect the corresponding echo signals, there is a need to be able to use such techniques with older less sophisticated ultrasound machines or with machines that are not specifically designed to support a photoacoustic imaging mode. The disclosed technology is a laser light source that can be used with conventional ultrasound imaging machines to allow them to implement photoacoustic imaging to show the location of an interventional instrument tip in a body.

DETAILED DESCRIPTION

Figure 1A:
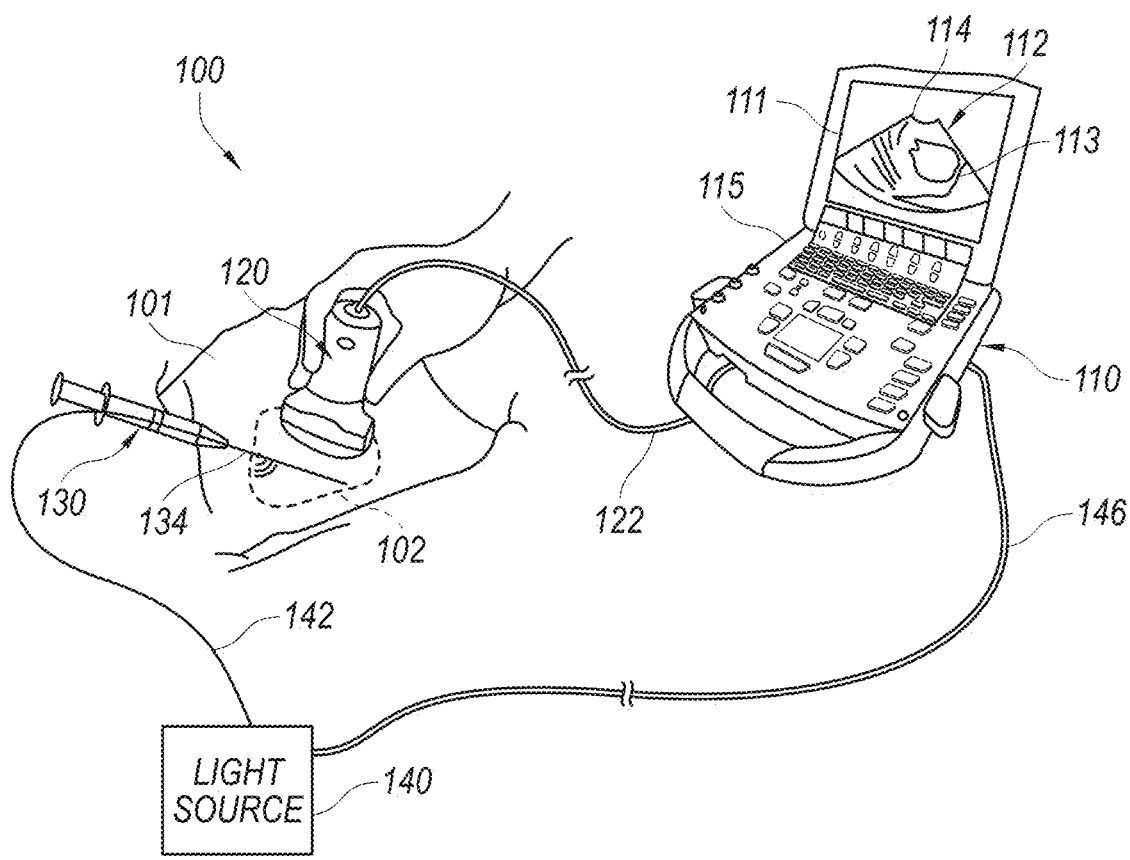
FIG. 1A illustrates an interventional instrument imaging system configured in accordance with an embodiment of the disclosed technology.

The disclosed technology relates to systems and methods for facilitating interventional procedures such as, for example, the administration of anesthesia, MSK/sports medicine for joint/tendon/muscle injections, fine needle aspiration, amniocentesis, thoracentesis, pericardiocentesis, vascular access and biopsy. In one embodiment, a system includes an ultrasound imaging machine and an external laser light source that communicates with the ultrasound imaging machine to deliver light pulses to an interventional instrument (e.g., a needle, a catheter, a biopsy instrument, guidewire, vascular filter or the like). The ultrasound imaging machine is configured to transmit ultrasound energy into a region of interest of a subject (e.g., a human or an animal) and receive corresponding ultrasound echoes from the subject and the instrument. The laser light source generates one or more laser light pulses that are transmitted to a tip or a distal portion of the interventional instrument via one or more optical fibers. The distal end of the one or more fibers is covered with a light absorbing material such as a black epoxy. The laser light pulses are absorbed by such material in an area adjacent the distal tip of the interventional instrument, which causes photoacoustic signals to be produced.

In one embodiment, the light absorbing material absorbs the laser light pulses and emits corresponding photoacoustic signals that the ultrasound imaging machine can detect. The ultrasound imaging machine receives the photoacoustic signals and produces real-time line data for use in creating an ultrasound image of the tip of the interventional instrument based on the detected photoacoustic signals. In some embodiments, the ultrasound imaging machine is configured to produce an ultrasound image of the tip of the interventional instrument using a color map. The ultrasound imaging machine can process the photoacoustic signals to form a colorized ultrasound image that is superimposed on, or combined with, a normal gray-scale tissue image. As a result, the user can visualize a colored set of pixels that is the ultrasound image showing the tip of the interventional instrument in real time. The ultrasound imaging machine can be configured to receive a user command to turn this feature on/off and to control the intensity or brightness of the colored image via gain or laser output power manipulation within the allowed regulatory requirements. The machine can also be configured to receive user input regarding a desired color for the displayed image of the instrument tip. In some embodiments, a signal to turn on the imaging mode is sent from the external laser light source when an optical fiber is connected automatically to facilitate and reduce or simplify the user interaction. These and other embodiments of the disclosed technology are expected to provide more natural hand-eye coordination, more precise placement of the interventional instrument tip, reduced procedure times and/or enhanced visualization of the location of the instrument compared to conventional instrument visualization techniques. This is especially helpful for steep angle insertions where it has been difficult to image a needle using traditional ultrasound imaging techniques. For out-of-plane insertions, the disclosed technology can tell the user if a needle tip has reached the imaging plane.

Figure 1B:
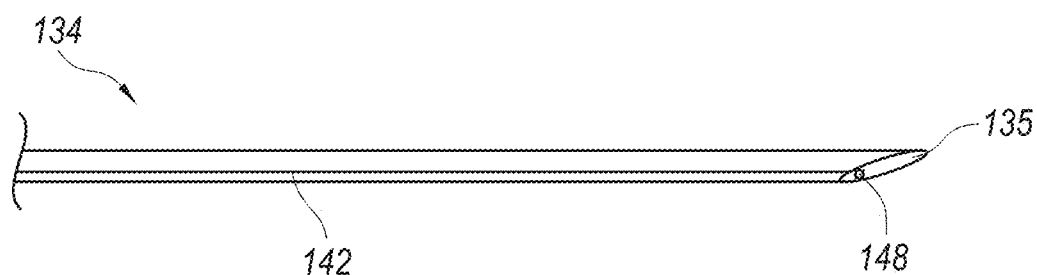
FIG. 1B illustrates one embodiment of a needle for use with the interventional instrument imaging system shown in FIG. 1A.

FIG. 1A is a partially schematic view of an embodiment of an interventional instrument imaging system 100 including an ultrasound imaging machine 110 coupled to an ultrasound transducer 120, an external laser light source 140 and an interventional instrument 130 (e.g., a needle). FIG. 1B is a schematic view of a shaft portion 134 of the interventional instrument 130. Referring to FIGS. 1A and 1B, the ultrasound transducer 120 is configured to transmit ultrasound energy into a region of interest 102 of a subject 101 and receive corresponding ultrasound echoes from the region of interest 102. A cable 122 carries electronic signals produced in response to the received ultrasound echoes from the transducer 120 to the ultrasound imaging machine 110. The ultrasound imaging machine 110 processes the electronic signals and generates one or more ultrasound images 113 that are displayed on a user interface 112 of a display 111. An input interface 115 receives user input and instructions via one or more user input controls (e.g., one or more buttons, keys, knobs, switches, sliders, trackballs and/or touch-sensitive surfaces).

Figure 1C:
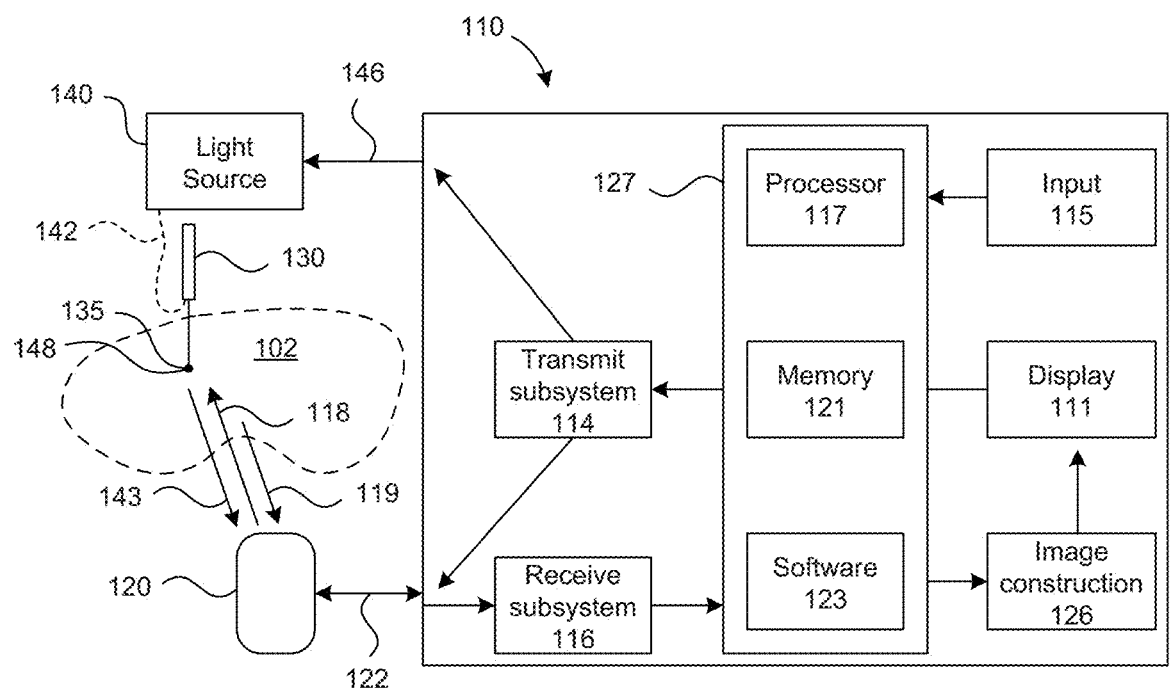
FIG. 1C is a functional block diagram of an ultrasound imaging machine of FIG. 1A during a photoacoustic imaging procedure in accordance with an embodiment of the disclosed technology.
Figure 1D:
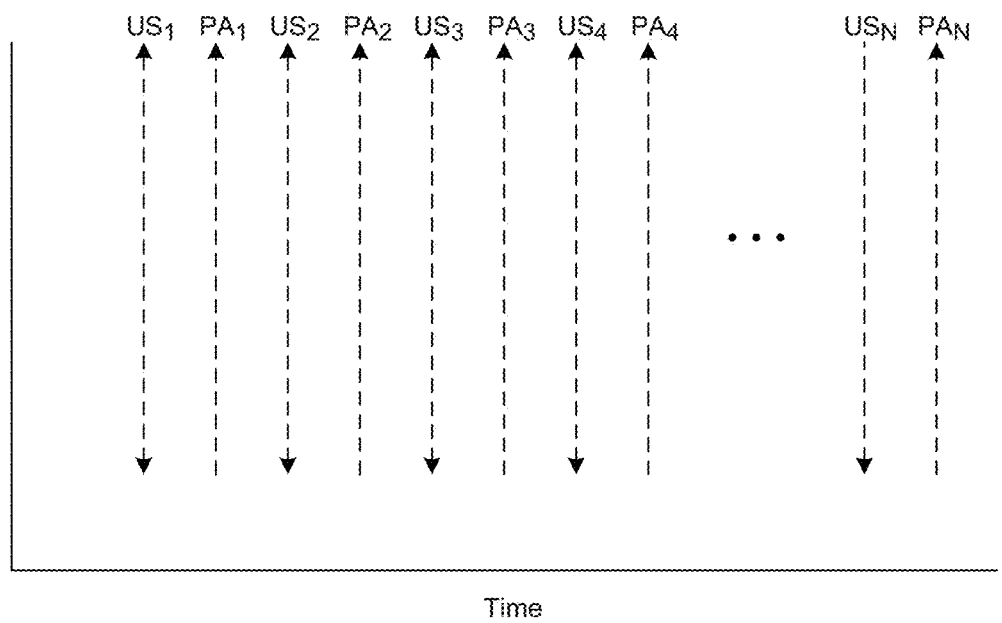
FIG. 1D is a timing diagram showing an example of a transmission and receiving sequence of interleaved ultrasound and photoacoustic line signals in accordance with one embodiment of the disclosed technology.

Referring to FIGS. 1A-1C together, the external laser light source 140 (including a laser diode, miniaturized YAG, Alexandrite or other type of laser light source) communicates to a port such as an EKG port, on the ultrasound imaging machine 110 via a connection cable 146 (e.g., a USB cable, I2C cable, EKG cable, an HDMI cable or a custom designed cable). In some embodiments, however, a wireless connection (e.g., Bluetooth, 802.11 etc.) can be used for communication between the external laser light source 140 and the ultrasound imaging machine 110. One or more optical fibers 142 extend from the laser light source 140 to a tip 135 (FIGS. 1B and 1C) of the shaft 134. In some embodiments, the one or more optical fibers 142 extend through an interior portion of the shaft 134. In other embodiments, however, the one or more optical fibers 142 extend on an exterior surface of the shaft 134. In another embodiment, two or more channels of the needle could be used to house the fiber specifically. The one or more optical fibers 142 can be attached to the interior or the exterior surface of the shaft 134 with an epoxy or another adhesive to allow room for fluid flow inside the shaft of the interventional instrument 130. In some embodiments, a double or multi-lumen instrument separates the one or more optical fibers 142 from a fluid channel. In some embodiments, the exterior of the shaft 134 is free of markers, while in other embodiments an outer surface of the shaft includes one or more markers that are used to indicate the depth to which shaft is inserted into a body.

As will be explained in further detail below, in some embodiments, the laser light source 140 includes a system interface for power and communication, a memory for storing a device ID and program instructions, an optical assembly including a mechanical connector for engaging a fiber optic connector, a light shutter, a light ring and one or more LEDs that illuminate when light source is powered and the laser is activated.

The external laser light source 140 is configured to produce one or more fixed or variable wavelength laser light pulses in the range of visible or invisible IR light (300 nm to 1500 nm) as an example, that are transmitted to the tip 135 of the interventional instrument via the one or more optical fibers 142. The duration of the laser pulses is selected so that the photoacoustic signals created at the tip of the instrument are in the receive bandwidth of the ultrasound transducer 120.

In some embodiments, a light absorbing medium 148 (FIG. 1B) is positioned at the tip 135 and covers the ends of the one or more fibers. The light absorbing medium absorbs the one or more laser light pulses transmitted from the laser light source 140 and generates photoacoustic signals 143 (FIG. 1C). As shown in FIG. 1C, the ultrasound transducer 120 transmits ultrasound pulses 118 into a region of interest and detects ultrasound echoes 119 as well as the photoacoustic signals 143 that are created in response to the laser pulses. As explained in further detail below, the ultrasound imaging machine 110 produces data for one or more ultrasound images of tissue and the interventional instrument 130 in the region of interest 102 using the detected ultrasound echoes 119 and the photoacoustic signals 143. As those of ordinary skill in the art will appreciate, because the photoacoustic signals 143 originate only from the tip of the instrument, the source of the photoacoustic signals 143 is the tip location. The ultrasound imaging machine 110 creates data for two images (e.g. from the returned ultrasound echoes and the received photoacoustic signals respectively), and combines the data for both images to create a color image of the tip of the instrument on the normal gray scale tissue image that is shown to the user. In some embodiments, the image of the tip is colorized differently from a traditional gray scale ultrasound tissue image to increase the contrast or awareness of the tip location. Note the photoacoustic image is an ultrasound real time image created in response to photoacoustic signals that originate directly from the location of the instrument tip, not a graphical indicator that is derived from some other inputs. Therefore, the creation of the image is not affected by bending of a needle shaft and is applicable for any angle of insertion including an out-of-plane insertion.

In some embodiments, the light absorbing medium 148 at the distal end of the instrument comprises an epoxy that absorbs the laser light pulses and emits corresponding photoacoustic signals 143 (FIG. 1C). Because the photoacoustic signals 143 are only emitted from the tip 135, the ultrasound imaging machine can produce an image of the tip 135 directly without using another method to infer the location of the shaft 134 and/or the tip 135.

In some embodiments, the light absorbing medium 148 may comprise, for example, an epoxy, a polymer, a plastic and/or another suitable material for that absorbs the laser light and generates the photoacoustic signals. One benefit of using a light absorbing material is prevention and/or reduction of light leakage into the tissue that itself could generate photoacoustic signals, which could cause ambiguity of the needle tip location. In other embodiments, the ends of the one or more optical fibers are silvered or otherwise coated with a metal that absorbs the laser pulses. In still other embodiments, the optical fibers are angled, cut or lensed so that the laser light pulses are directed onto the distal end of the interventional instrument or into the tissue. The material that absorbs the pulses then generates the photoacoustic signals in a manner that is similar to that of the black epoxy.

Figure 2:
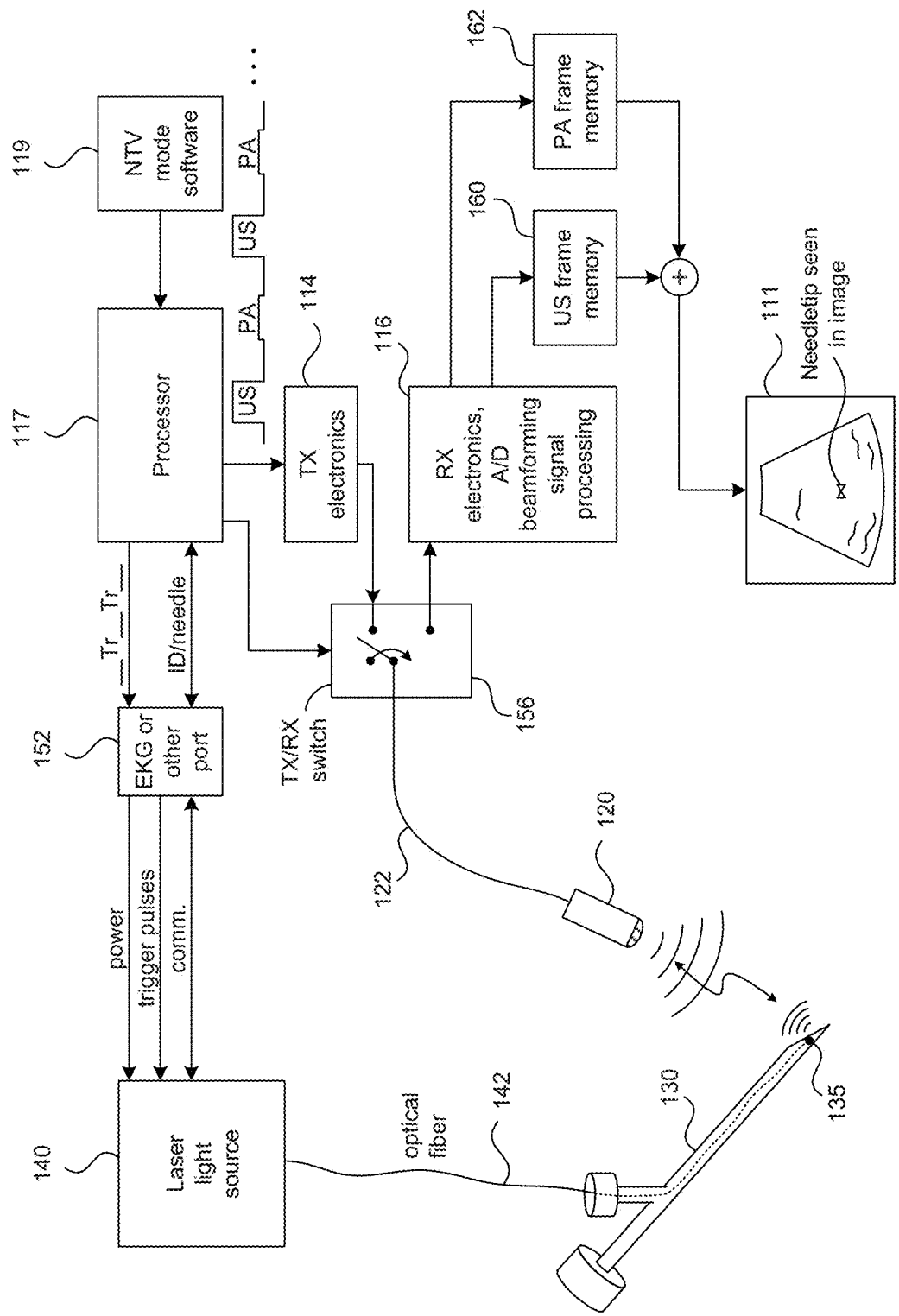
FIG. 2 is a functional block diagram of an ultrasound imaging machine designed to produce an image of a tip of an interventional instrument using photoacoustic signals in accordance with some embodiments of the disclosed technology.

FIG. 2 illustrates further detail of one embodiment of an ultrasound imaging machine that is programmed to produce images of an instrument tip using the photoacoustic signals. The ultrasound imaging machine includes one or more processors 117 that are programmed to execute needle tip visualization (NTV) software when an operator wants to visualize the position of a needle using photoacoustics. After connecting the external laser light source 140 to a port (EKG, USB or other port) 152 on the ultrasound machine, the laser light source 140 communicates a device ID to the processor 117 to inform the machine that the laser light source 140 is connected. In one embodiment, power for the external laser light source 140 is provided from the ultrasound machine through the port 152. However, the laser light source 140 could be powered by a battery or from another power source if desired.

As indicated above, some ultrasound imaging machines do not have the specialized hardware needed for photoacoustic imaging (also referred as a needle tip visualization mode—NTV). For these ultrasound machines, the operating software is modified so that the ultrasound machine can produce data for two images that are blended together where some of the data is created from the received photoacoustic signals. In accordance with one embodiment of the disclosed technology, when operating in the NTV mode, the processor 117 executes NTV software instructions 119 that cause the processor 117 (or the transmit electronics 114) to generate a trigger signal (labelled Tr) when the laser light source 140 is to produce a laser light pulse. In some embodiments, the processor 117 also instructs the transmit electronics 114 to reduce the amplitude or the length of a transmit pulse at those times when a laser light pulse is produced by the external laser light source so that minimal or preferably no ultrasound energy is produced by the ultrasound transducer 120. Minimal energy is energy that is sufficiently small enough such that it does not interfere with the detection of the photoacoustic signals at the ultrasound transducer. Upon receipt of the trigger signal, the external laser light source produces one or more laser pulses, which cause photoacoustic signals to be generated near the needle tip. Receive electronics 116 in the ultrasound system 110 are then enabled to detect the photoacoustic signals.

A transmit/receive switch 156 is used to protect the sensitive receive electronics 116 from the large voltages produced by the transmit electronics 114 and other transients. After one or more pulses have been transmitted by the ultrasound transducer 120 for the acquisition of a line for a B-mode imaging frame, the position of the transmit/receive (T/R) switch 156 is changed by the processor 117 so that the receive electronics 116 begin detecting the return echo signals from a desired distance away from the transducer (e.g. the skin line). During a photoacoustic line acquisition, the transmit/receive switch 156 is controlled by the processor 117 so that the receive electronics begin receiving signals from the same positions away from the transducer as the lines in the ultrasound frame. In some embodiments, it was found that closing the T/R switch causes transients that are detected by the receive electronics. Therefore, in some embodiments, the position of the T/R switch 156 remains closed after obtaining a B-mode line while the photoacoustic signals are obtained until such time as the ultrasound imaging system supplies ultrasound signals to the transducer for the creation of the next B-mode ultrasound line.

Echo signals created in response to the B-mode firings are beamformed and signal processed and may be stored in a B-mode image frame memory 160 until all the line data required to produce a frame are obtained. Similarly, beamformed and signal processed photoacoustic signals may be stored in a second image frame memory 162 (labelled photoacoustic PA memory). Once all the line data for both image frames are obtained, the processor 117 combines data from each imaging mode to produce data for a composite image in which the tissue in the region of interest and the position of the distal end of the interventional instrument can be seen.

As indicated above, because the ultrasound imaging machine 110 is not specially designed to perform photoacoustic imaging, the machine uses the existing receive electronics 116 to process the photoacoustic signals. In addition, in one embodiment, the machine is programmed to operate as if it transmits ultrasound from the imaging transducer but the transmit electronics 114 are controlled to transmit pulses with minimal or no energy by reducing the amplitude of the pulses to zero or by setting their pulse length to zero. In this embodiment, the ultrasound system behaves as if it is transmitting ultrasound into the body and detecting the corresponding echo signals when in fact the signals are photoacoustic signals generated in response to the one or more laser pulses. These laser pulse firings are synchronized with the transmission of the minimal energy signals.

For photoacoustic imaging or NTV mode, the processor 117 sends or causes other electronics to send a trigger signal to the external laser light source 140 each time a laser pulse is requested (coinciding when the transmitter is programmed to transmit pulses with zero or minimal energy) for each or multi-receive lines. The laser light source 140 receives the trigger signal and fires the laser.

Further details of how the ultrasound imaging machine 110 operates to produce an image of the distal tip of the interventional instrument from the received echo signals and the photoacoustic signals are found in commonly owned U.S. patent application Ser. No. 15/612,634 (titled "Method and Apparatus for Visualizing A Medical Instrument Under Ultrasound Guidance"), which is filed concurrently herewith and is incorporated by reference in its entirety.

External Laser Light Source

Figure 3A:
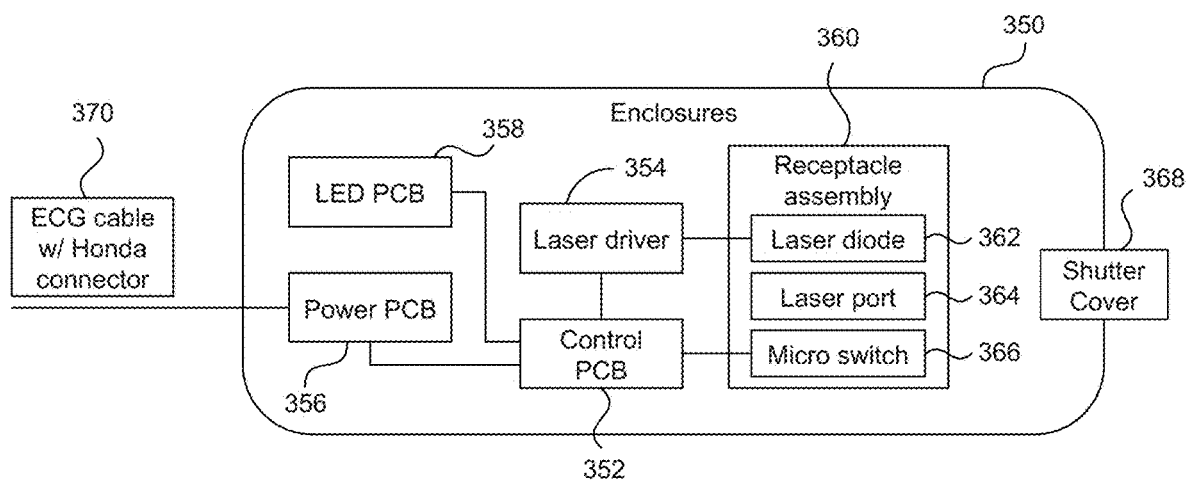
FIG. 3A is a functional block diagram of an external laser light source in accordance with an embodiment of the disclosed technology.
Figure 3B:
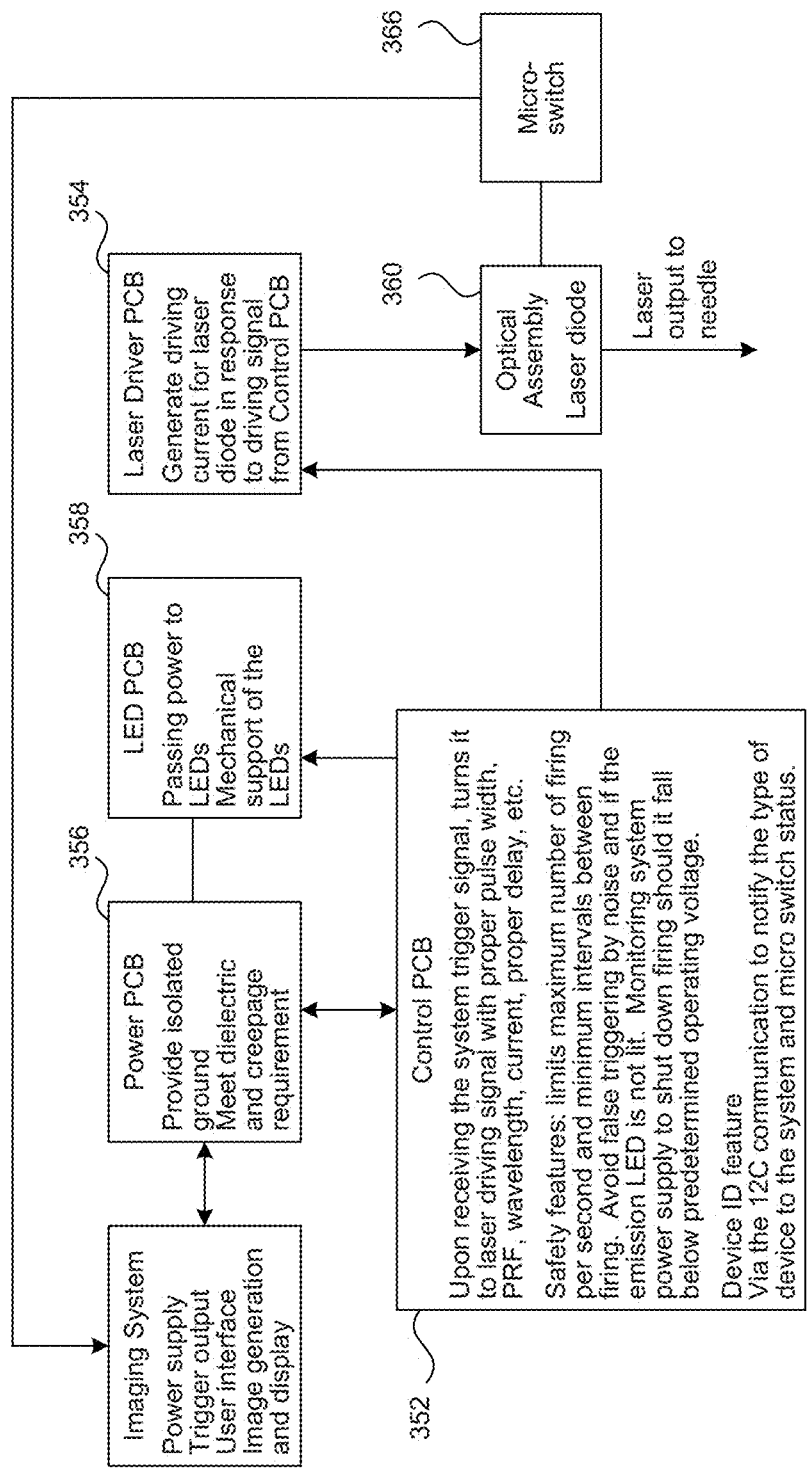
FIG. 3B illustrates various functions performed by different printed circuit boards in the external laser light source.

FIG. 3A is functional block diagram of an external laser light source. In the embodiment shown, the laser light source includes three printed circuit boards: a control board 352, a laser driver board 254, a power board 356 and an optical assembly 360. As shown in FIG. 3B, the power board 356 is configured to receive a supply voltage from a connected ultrasound imaging machine and provide the appropriate voltage levels to run the circuitry in the laser light source. The control circuit board 352 includes logic such as an FPGA or a processor with an external or built-in memory that is configured to communicate with the attached ultrasound imaging machine and to receive the trigger signals that cause the laser to fire. The laser driver board 354 is configured to receive control signals from the control board 352 and supply the appropriate driving signals to the laser source to produce laser pulses when requested. In one embodiment, the external laser light source is configured to communicate with the connected ultrasound imaging machine using the I2C communication protocol via a cable that is connected to an EKG port on the ultrasound system. However, other wired or wireless communication protocols and ports could be used.

The optical assembly 360 is configured to receive a standardized style of fiber optic connector having one or more optical fibers that extend to the distal tip of an interventional instrument (e.g. a needle). The optical assembly 360 includes a laser diode, an optical coupler and lens (not shown) that directs light from the laser diode into one or more connected optical fibers. In addition, one embodiment of the optical assembly includes a micro-switch 366 that changes state when an optical connector (not shown) is inserted into the optical assembly. In some embodiments, the optical assembly 360 also includes a mechanical or optical shutter 368 that covers the output of the laser diode when no optical fibers are connected and otherwise prevents laser light from being transmitted outside of the light source. An LED printed circuit board 358 supports a number of LEDs that are illuminated depending on the operating condition of the laser light source as will be described.

Figure 3C:
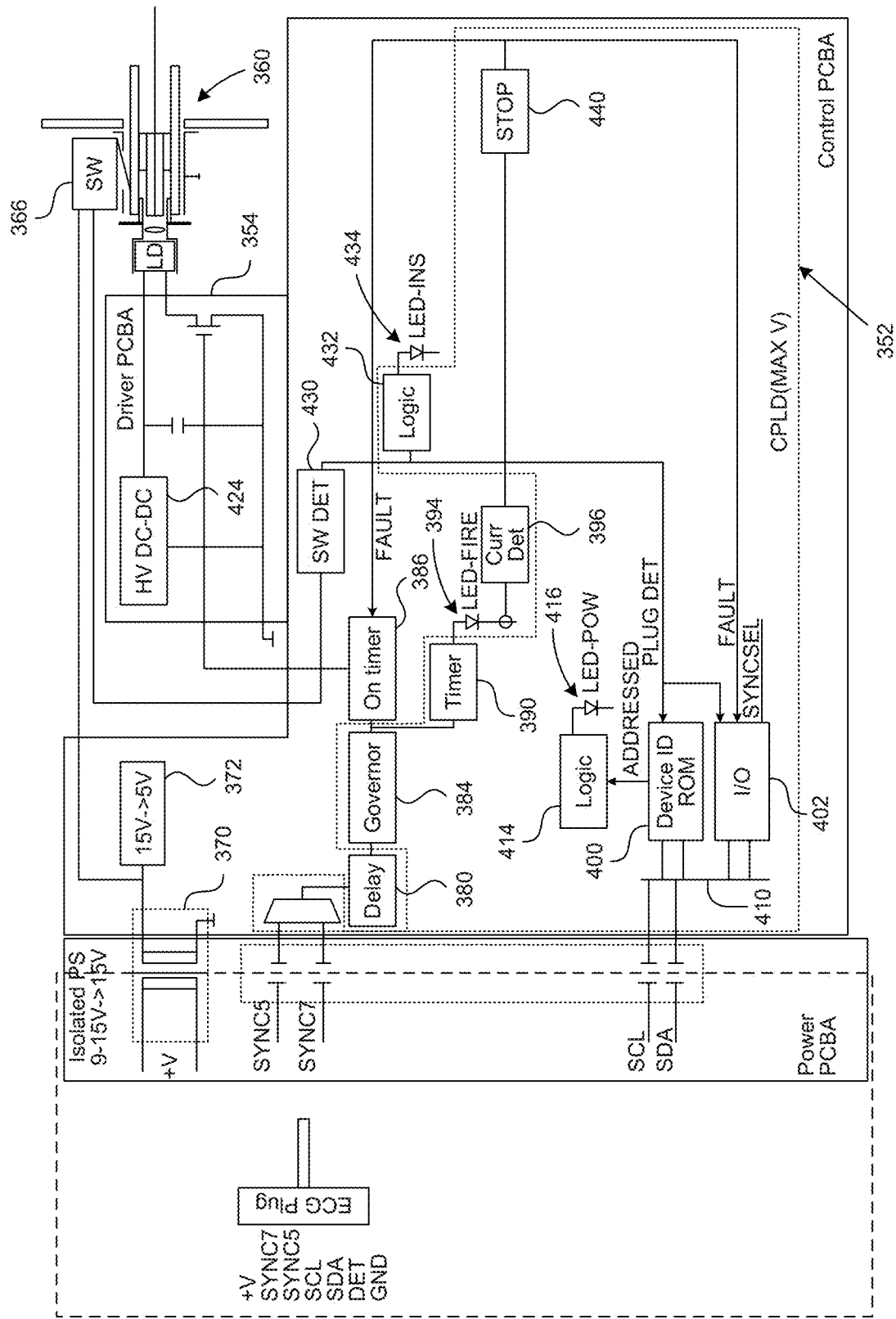
FIG. 3C is an electrical block diagram of the external laser light source in accordance with an embodiment of the disclosed technology.

FIG. 3C is an electrical block diagram showing the operation of the external laser light source. In one embodiment, the laser light source includes a connector to connect with +V, Sync7, Sync5, SCL and SDA I2C lines, DET and GND pins on an EKG port of the ultrasound imaging system. The +V connection is passed through an isolating transformer 370 to a voltage regulator 372 that converts the voltage received to the appropriate voltage level needed to run circuitry on the control board.

A delay or blanking circuit 380 receives a trigger signal over a communication channel from the ultrasound imaging machine on the Sync7 or Sync5 lines of the EKG port. The delay or blanking circuit 380 operates as a momentary gate to prevent further signals from being detected after a trigger signal is received as will be explained in further detail below. An output of the delay or blanking circuit 380 is fed to a governor circuit 384 that serves to limit the time between successive laser pulses and the maximum number of laser pulses that can be produced in a predetermined time limit (e.g. 1 minute) to levels required by safety regulations. The governor circuit 384 prevents successive laser pulses from being fired too close together and counts the total number of laser pulses to be fired in the time limit. Laser firings are delayed if successive trigger signals are received in too short a time and the governor circuit 384 can prevent additional laser firings once the total number of laser firings reaches the number permitted in the predetermined time period. The output of the governor circuit 384 feeds a timer circuit 386 that provides a driving signal of the appropriate duration to the laser driver board 354 in order to turn on a transistor that allows current to flow through the laser diode in order to produce the desired laser pulse.

The output of the governor circuit 384 also feeds a timer circuit 390 that drives an LED 394 to indicate when the laser is firing. The timer 390 drives the LED 394 to visually indicate to an operator that a laser pulse is firing The timer 390 is set so that the LED 394 remains illuminated for longer than the driving pulse in order to make the LED visible instead of briefly flickering each time the laser is fired.

In one embodiment, the delay or blanking circuit 380, the governor 384 and timers 386 and 390 are implemented as logic functions in an FPGA circuit. However it will be appreciated that such functions could also be performed by software executed by a processor on the control circuit board or with discrete digital or analog circuitry.

In some embodiments, the firing of the laser light source generates electronic noise that can be mistaken for a trigger signal at the input communication lines. The delay or blanking circuit 380 described above prevents this noise from triggering another laser pulse by limiting any additional signals on the communication lines from passing to the governor circuit 384 for a period of time after each trigger signal is received. For example, the delay or blanking circuit 380 may act as a switch that opens for a period of time upon receipt of a trigger signal and closes at a time when any interfering noise will have dissipated.

In the embodiment shown, the control board 352 also includes a memory 400 and an I/O circuit 402 that are connected to a common I2C bus 410. Bus 410 is connected through a capacitive isolation circuit to the SCL and SDA I2C communication pins of the EKG port. A logic circuit 414 controls an LED power indicator 416 to illuminate when the external laser light source is connected to the ultrasound imaging machine.

The external laser light source has several built in safety circuits. In the disclosed embodiment, the V+ power is routed through the micro-switch 366 (FIG. 3A) that changes state when an optical connector is inserted into the optical assembly 360. Closing the micro-switch 366 passes the V+ power received from the ultrasound machine to a high voltage DC-DC converter circuit 424 on the laser driver board 354 that increases the voltage to a level sufficient to drive the laser diode. In addition, with the micro-switch 366 closed, the voltage V+ appears at a switch detect circuit 430 that provides an output indicative of whether the micro-switch 366 is opened or closed. The output of the switch detect circuit 430 drives a logic circuit 432 that turns on an LED 434 to indicate that an optical connector has been inserted into the optical assembly of the laser light source. In some embodiments, a detector (not shown) can monitor the driving voltage applied to the laser diode to produce a signal that can shut the laser light source down if not in a desired range. In addition, a current detector (not shown) can be placed in line with the laser diode and the current integrated over time and compared to a limit as an estimate for laser light power transmitted.

The output of the switch detect circuit 430 also is applied to the memory circuit 400 to set the address by which the memory 400 can be accessed. With the output of the switch detect circuit in one state, the memory 400 is accessed at a first address and when the output the switch detect circuit 430 is in the opposite state, the memory 400 is accessed at another address. The connected ultrasound imaging machine can therefore determine if an optical assembly is inserted into the laser light source by determining which address can access the memory 400.

In another or the same embodiment, the I/O circuit 402 detects the output of the switch detect circuit 430 and sends a signal to the connected ultrasound imaging machine using the I2C communication protocol.

A stop circuit 440 receives the output of the switch detect circuit 430 and the output of a current detect circuit 396 that is connected to the LED 394, which is illuminated when the laser is firing. The stop circuit 440 produces a logic signal indicative of whether an optical connector is inserted into the laser light source AND if the LED that indicates that laser pulses are being fired is illuminating. If either condition is not true, then a stop signal is generated that is fed back to the timer circuit 386 to halt laser pulse firings, In addition, the stop signal can be supplied to the I/O circuit 402 to signal the connected ultrasound imaging machine that a fault or other condition has occurred and that no laser pulses are permitted to fire.

Figure 3D:
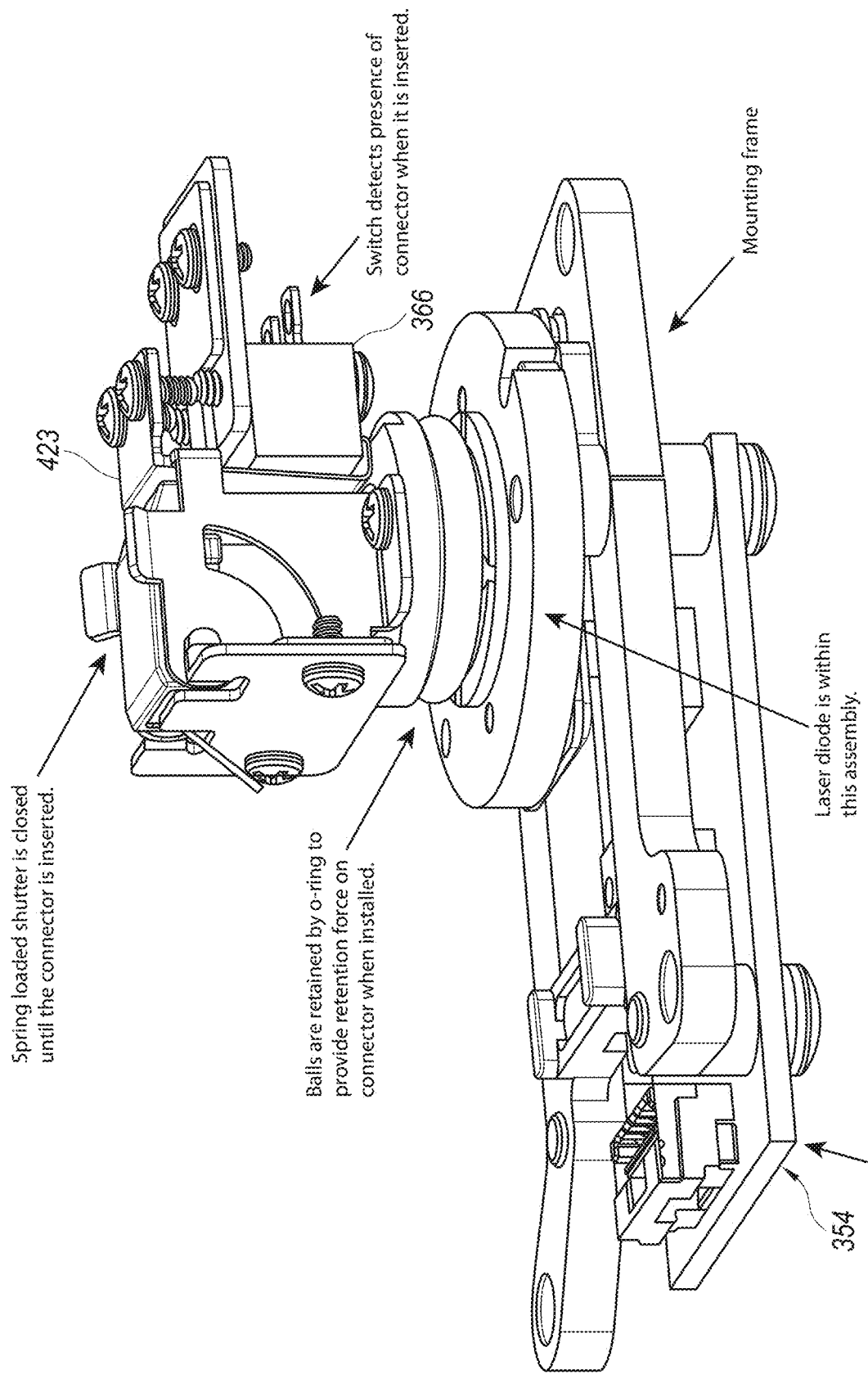
FIG. 3D illustrates additional detail of the laser light source that includes a mechanical shutter, an optical assembly, a micro-switch, and a fiber optic connector used in the external laser light source.

FIG. 3D shows some additional detail of the optical assembly that is mounted on the laser driver printed circuit board 354. A mounting frame is secured to the laser driver board and supports the optical assembly including the laser diode and lens (not separately shown). A spring loaded optical shutter is configured to move out of the way of the laser diode when an optical connector (not shown) is inserted into the optical assembly and to block the output of the laser diode when the optical connector is removed from the optical assembly. The micro-switch 366 is closed by a plate 423 that is moved when the optical connector is inserted into the optical assembly.

Figure 3E:
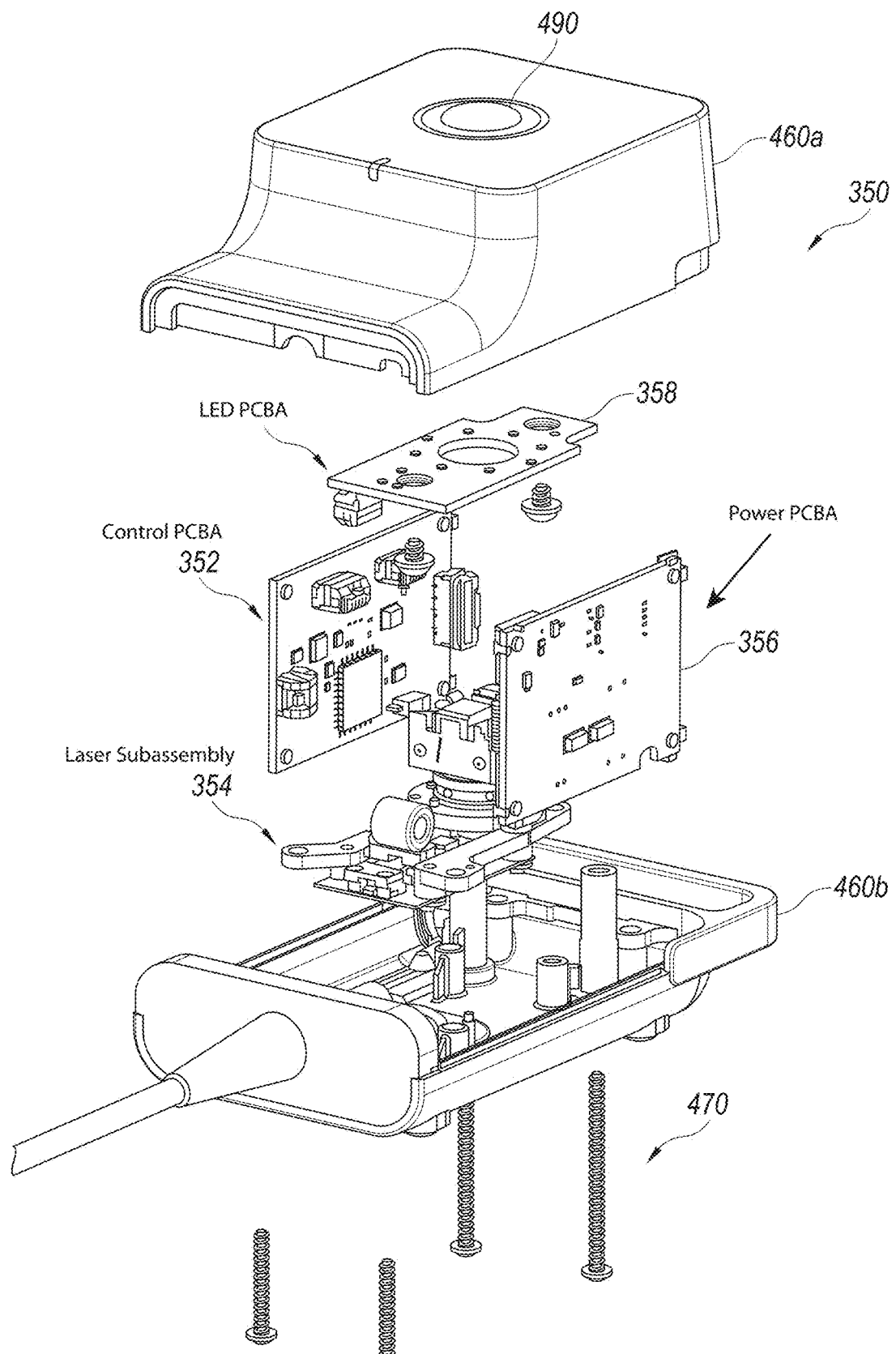
FIG. 3E is an exploded view of the external laser light source shown in FIG. 3A in accordance with an embodiment of the disclosed technology.

FIG. 3E is an exploded view of an enclosure 350 for the external laser light source with a top cover 460a separated from a bottom cover 460b. The cover 460 surrounds and supports the printed circuit boards of the laser light source as well as the optical assembly. The top and bottom covers 460a, 460b are held together with screws 470 or other fasteners. In one embodiment, the top cover 460a includes a flexible rubber seal 490 having a cross-shaped slit therein that allows a fiber optic connector to be inserted into the optical assembly while limiting the ability of cleaning or other fluids to enter the enclosure.

Figure 3F:
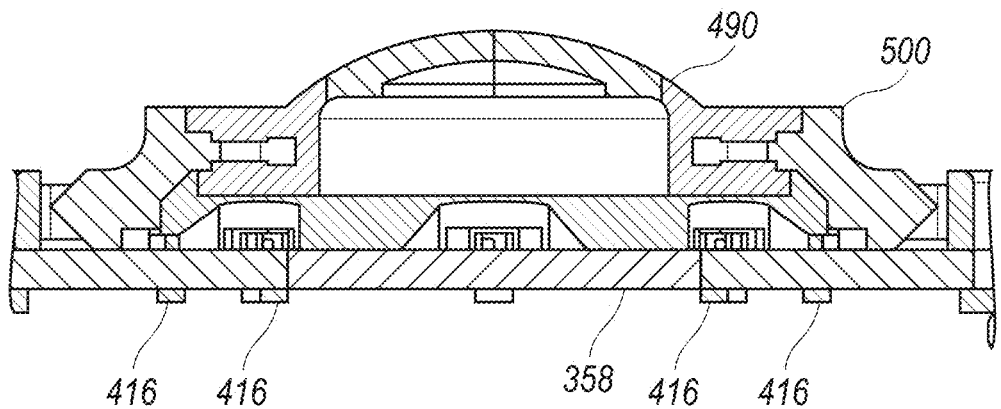
FIG. 3F is an cross-sectional view of a flexible seal and a light ring in the external laser light source in accordance with an embodiment of the disclosed technology.
Figure 3G:
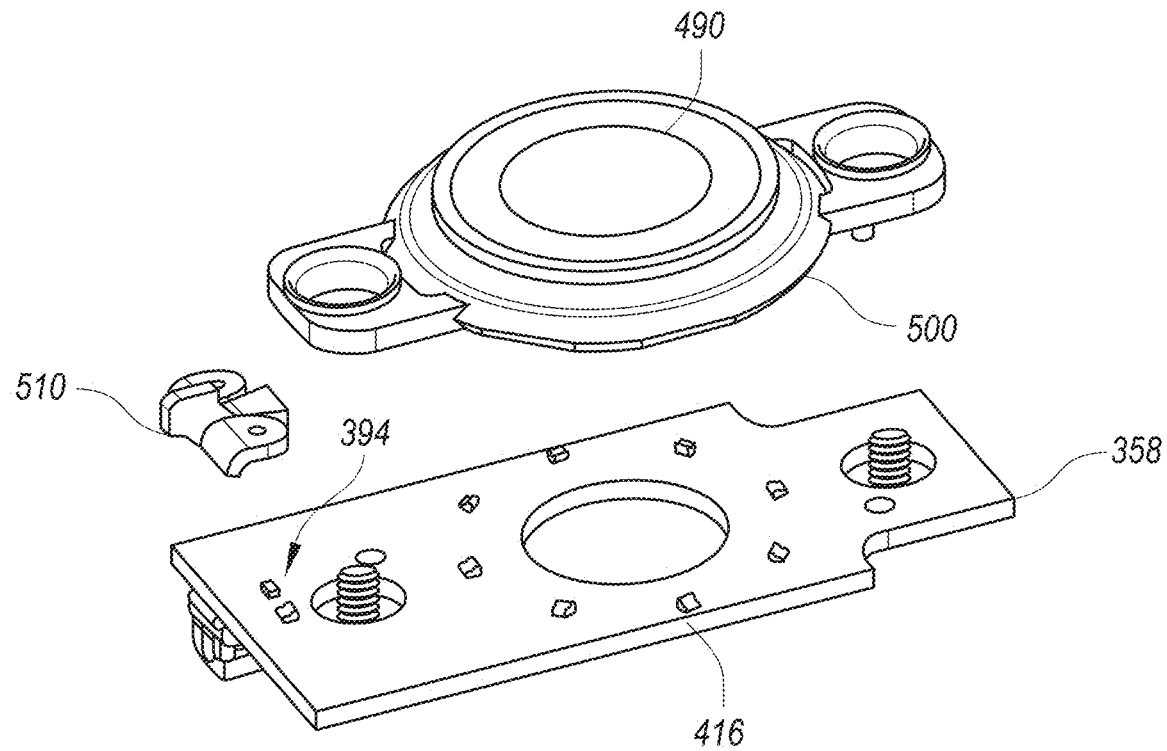
FIG. 3G is an exploded view of a flexible seal and a light pipe with a printed circuit board in accordance with an embodiment of the disclosed technology.

FIG. 3F is a cross-sectional view of the flexible rubber seal 490 in the external laser light source. In one embodiment, the flexible seal 490 is a circular, dome-shaped rubber seal that is molded over a light ring 500 that surrounds the perimeter of the seal. The dome shape of the seal allows liquids to flow away from the slits in the rubber seal thereby limiting the ability of liquids to enter the enclosure of the laser light source. One or more LEDs on the LED driver printed circuit board 358 illuminate the light ring 500 around the seal when the laser light source 350 is connected to the ultrasound imaging machine so that a user can easily see when the device is powered. Also shown in FIG. 3G is an LED 394 that indicates when the laser light source is firing.

The LED 394 is coupled to a light pipe 510 that terminates on an exterior portion of the top cover 460a.

Figure 3H:
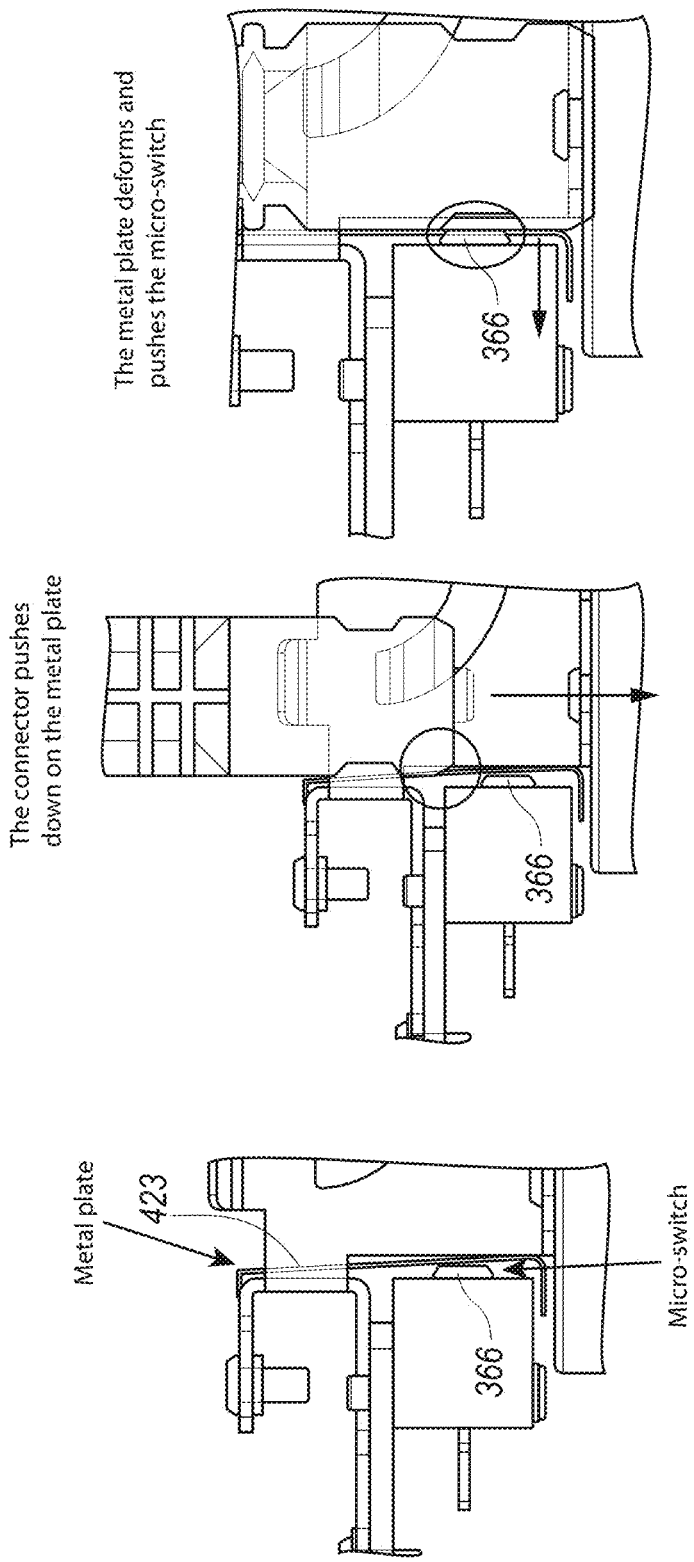
FIG. 3H illustrates a micro-switch that changes stated upon the insertion of a fiber optic connector to an optical assembly in accordance with an embodiment of the disclosed technology.

FIG. 3H shows additional detail of the micro-switch 366 that is in the optical assembly. The plate 423 is pressed against the micro-switch 366 when an optical connector is inserted in the optical assembly. As indicated above, in one embodiment, closing the micro-switch 366 causes a signal to be sent to the ultrasound imaging machine or changes the address of the memory that can be read to indicate that an optical connector has been inserted into the optical assembly. In one embodiment, the ultrasound imaging machine enters a needle tip visualization mode when it detects that an optical connector has been inserted into the optical assembly. In this way, a user can cause the ultrasound imaging machine to begin operating in the NTV mode simply by plugging in a fiber optic connector without having to use separate controls on the ultrasound machine.

Figure 3I:
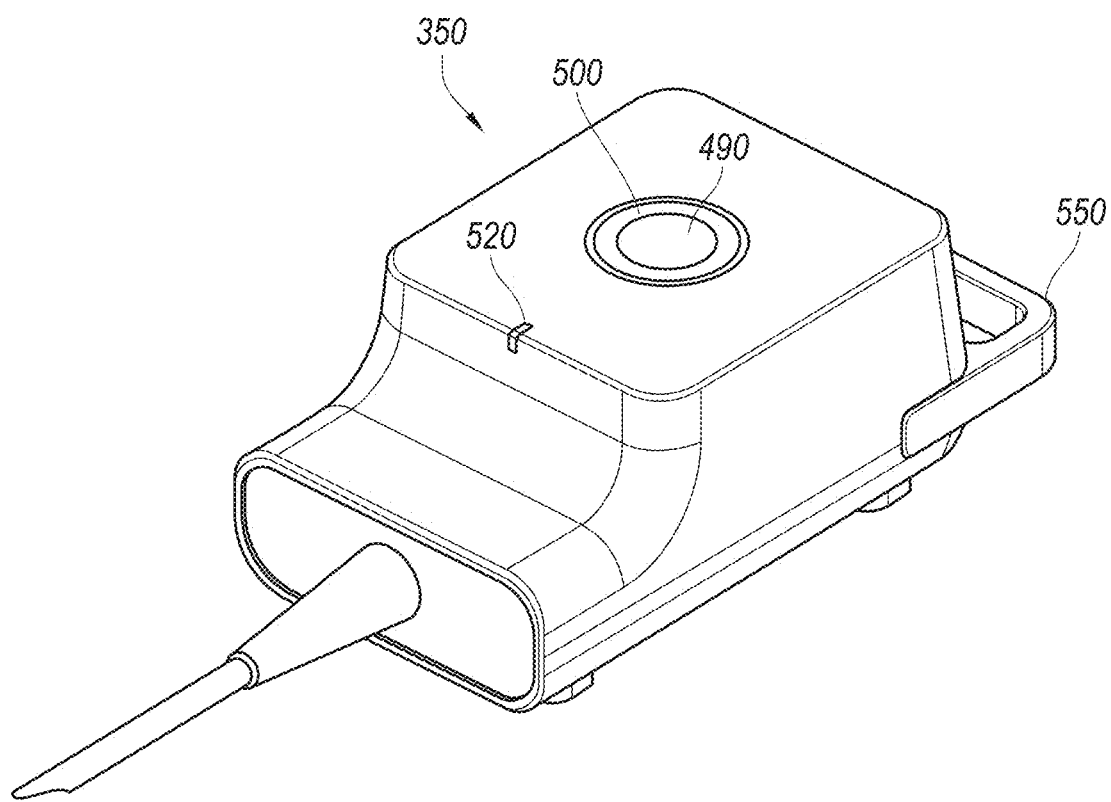
FIG. 3I is an isometric view of the external laser light source constructed in accordance with an embodiment of the disclosed technology.

FIG. 3I is an isometric view of the housing 460 for the external laser light source. At the center of the top cover 460a is the flexible dome-shaped seal 490 surrounded by the light ring 500 that is illuminated when the laser light source is connected to an ultrasound machine. An end of the light pipe 510 is positioned on the top cover 460a between the flexible seal 490 and a cord that connects the laser light source to the ultrasound imaging machine. As indicated above, the light pipe 510 is illuminated when an optical fiber is inserted into the optical assembly and when the laser diode is firing. A ring or loop 550 is provided at one an end of the laser light source housing 460 that allows the laser light source to be hung from a hook on an ultrasound supply cart or the like. In one embodiment, the laser light source housing is approximately the size of a deck of playing cards and is small enough to fit in a receptacle that is typically used to store transducers or gel on a ultrasound cart. A hook attachment could also be designed to be attached to the main ultrasound machine stand column to store the laser light source box. The housing of the laser light source is generally free of sharp corners to make it comfortable to hold and easy to keep clean.

In some embodiments, the housing of the laser light source can optionally include other attachment mechanisms (e.g., a flexible clip, clamp, magnet etc.) (not shown) as an alternative to the loop 550 to allow the device to be secured to a patient bed or other fixture to prevent droppage.

In one embodiment, the bottom surface of the laser light source housing has a rubber or other slip resistant rough surface (not shown) that prevents the laser light source from easily sliding off a surface.

As indicated above, the laser light source system is configured to produce laser pulses that are transmitted via the one or more optical fibers 142 to the tip 135 of the interventional instrument 130. Upon connecting the laser light source to the ultrasound imaging machine, the control board 352 is configured to generate or recall a device ID from a memory and transmits it to the connected ultrasound imaging machine over the communication link. The received device ID informs the ultrasound imaging machine that the connected unit is capable of producing laser pulses for needle tip visualization. Upon receipt of the device ID, the ultrasound machine activates the photoacoustic imaging mode. Once a user has inserted an optical fiber into the laser light source, the address of the memory is changed. In one embodiment, once the ultrasound imaging machine begins operating in NTV imaging mode, the machine begins trying to read the contents of the memory 400 at the two addresses address used when an optical connector is inserted into the optical assembly and the address used when an optical connector is not inserted into the optical assembly. Depending on which address allows the ultrasound imaging machine to read the memory 400, the ultrasound machine knows if a connector has been inserted into the optical assembly or not and can then begin sending trigger signals automatically at times when laser pulses are desired. This saves the trouble of turning the feature on/off manually, which is not convenient for a hand with sterile gloves on or requires an assistant's help.

As indicated above, the micro-switch 366 (FIG. 3H) is positioned so that it changes state when the user inserts the optical fibers into the optical assembly. If the optical fibers are purposely or accidentally removed from the laser light source, the micro-switch 366 changes state again and the address of the memory is changed and a stop signal is generated internally that causes the laser light source to cease producing laser light pulses.

In some embodiments, the micro-switch 366 can be replaced with another type of sensor (e.g., a relay, a Hall effect sensor etc.) in the optical assembly that detects proper connection of the one or more fibers 142. In certain embodiments, the software that initiates the photoacoustic imaging mode is configured to start a procedure upon the detection of an optical connector being inserted into the optical assembly without the operator having to use a sterile hand or to rely on a helper to initiate the procedure via the user interface.

Figure 4:
FIG. 4 is a representative screenshot of an ultrasound image that shows the distal tip of an interventional instrument in accordance with an embodiment of the disclosed technology.

Once the optical connector is inserted into the laser light source, the control board 352 monitors the communication link to the ultrasound machine for the trigger signals that indicate when laser pulses should be fired. Upon receipt of a trigger signal, the control board 352 causes the laser diode to fire one or more pulses into the connected optical fibers. As discussed above with reference to FIGS. 1A-1C and 2, the laser signals are absorbed by the light absorbing medium 148 at the end of the fibers, which generates corresponding photoacoustic signals that are detected by the ultrasound imaging machine 110. The ultrasound machine 110 uses the detected photoacoustic signals to form an ultrasound image of the tip 135 of the interventional instrument and the surrounding tissue FIG. 4 is a screenshot of an exemplary user interface 611 produced by the ultrasound imaging machine 110 (FIGS. 1A and 1C). The user interface 611 includes an ultrasound image 612 showing both tissue data 613 and a colorized tip ultrasound image 614 (e.g., the tip 135 of FIGS. 1A-1C). A plurality of user input controls 668 can be configured to receive a touch input from an operator to control various functions of the ultrasound imaging machine 110. Indicators 665 (identified individually as a first indicator 665a, a second indicator 665b and a third indicator 665c) provide visual cues that the external laser light source is connected and is powered (665a), has an optical fiber connected (665b) and is firing laser pulses (665c). In some embodiments, the ultrasound imaging machine 110 can be configured to provide one or more tactile, light, color change of the image 614 or/and audio feedback could confirm proper operation. In some embodiments, the color of the user interface on the ultrasound machine provides cues about the NTV accessory connected. For example, text in gray shows that the laser light source is connected and is executing the proper software version and the applicable transducer is present and the proper exam type has been selected. White lettering on the user interface indicates that the needle is present but the laser is not firing or the system is in freeze mode. Yellow lettering on the user interface indicates that the laser is firing. These color text indicators could be saved together with the image in an examination record.

In some embodiments, the ultrasound imaging machine 110 provides gain control for the colorized tip ultrasound image to provide the user a means to trade off the sensitivity with the noise. For example, for a deeper target the user might want to use a higher gain to boost the sensitivity but with more noise and artifacts. In one embodiment, the third indicator 664c is an indicator for the NTV gain control while 664a and 664b are for normal tissue and overall gain control.

The combined image includes image data corresponding to background tissue in the region of interest and a colorized image data corresponding to the tip of the interventional instrument. In some embodiments, the background tissue is shown in gray-scale while the image data corresponding to the tip of the interventional instrument is shown in an operator-desired color (e.g., red, yellow, blue, orange). In some embodiments, yellow is the preferred color for the pixels representing the tip of the interventional instrument because yellow is not generally associated with other ultrasound imaging modes and is easily seen by users—even those with red and green color impaired vision. Yellow and blue color blindness is very rare.

From the foregoing, it will be appreciated that specific embodiments of the invention have been described herein for purposes of illustration, but that various modifications may be made without deviating from the scope of the invention. Accordingly, the invention is not limited except as by the appended claims.

We claim:

1. A light source for use in photoacoustic imaging of an interventional instrument, the light source comprising:
   a housing external to an ultrasound machine and separate from a transducer of the ultrasound machine;
   a laser positioned in the housing;
   a first connector coupled to the laser that connects the light source to the ultrasound machine;
   a micro-switch positioned in the housing; and
   a control circuit positioned in the housing, comprising:
      a switch detect circuit coupled to the micro-switch to determine a state of the micro-switch when an optical connector is connected to the laser;
      and to transmit a switch signal indicating the state of the micro-switch through the first connector to the ultrasound imaging machine;
      a blanking circuit coupled to the laser that is configured to:
         receive a trigger signal that is sent from the ultrasound imaging machine in response to the switch signal; and
         control the laser to generate a laser pulse upon receipt of the trigger signal, wherein the blanking circuit is configured to receive trigger signals from the ultrasound imaging machine over a communication link through the first connector and to prevent the reception of additional trigger signals through the first connector for a period of time after the receipt of the trigger signal; and
      a memory coupled to the switch detect circuit, wherein an output of the switch detect circuit is applied to set a first address to access the memory when the state indicates that the optical connector is connected to the laser light source and to set a second address to access the memory when the state indicates that the optical connector is not connected to the laser light source.

2. The light source of claim 1, further comprising a stop logic circuit that is configured to produce a stop signal that halts the generation of laser pulses if the optical connector is removed from the light source.

3. The light source of claim 2, further comprising a light emitting diode (LED) that is illuminated when the laser is producing the laser pulses and wherein the stop circuit is configured to detect the operation of the LED and to produce the signal that halts the generation of laser pulses if the LED does not illuminate when a laser pulse is generated.

4. The light source of claim 1, wherein the control circuit is configured to send a device identification (ID) identifying the light source to the ultrasound imaging machine through the first connector.

5. The light source of claim 1, wherein the control circuit is configured to limit the rate at which the laser pulse is produced and a total number of laser pulses that are produced with a time limit.

6. The light source of claim 1, wherein the trigger signal is received at times when the ultrasound imaging machine is transmitting ultrasound signals with minimal or no energy.

7. The light source of claim 1, wherein the housing includes a dome-shaped rubber seal having one or more slits therein through which the optical connector is inserted.

8. The light source of claim 7, wherein the housing includes a light ring surrounding the dome-shaped rubber seal that is illuminated when the light source is connected to the ultrasound imaging machine.

9. The light source of claim 1, wherein the first connector is electrically coupled to the ultrasound imaging machine through a wired communication link.

10. The light source of claim 1, wherein the first connector is electrically coupled to the ultrasound imaging machine through a wireless communication link.

11. The light source of claim 1, wherein the optical connector is a fiber optic connector and wherein the switch signal indicates a first state of the micro-switch when the fiber optic connector is connected to the light source, and the switch signal indicates a second state when the fiber optic connector is not connected to the light source.

12. The light source of claim 1, wherein the control circuit is configured to prevent the reception of additional trigger signals for a period of time after the receipt of a trigger signal to enable noise due to firing the laser to dissipate and prevent the noise from triggering another laser pulse.

13. The light source of claim 1, wherein the communication link includes a first line and a second line, wherein the blanking circuit is connected to the first line to receive the trigger signal from the ultrasound machine, and the memory is connected to the second line for the ultrasound machine to access the memory on the second line.

14. The light source of claim 1, wherein the first address is to indicate to the ultrasound machine that the optical connector is connected to the laser light source and the second address is to indicate to the ultrasound machine that the optical connector is not connected to the laser light source.

15. A system for lighting an interventional instrument, the system comprising:

an ultrasound machine configured to generate trigger signals;
a laser light source configured to generate laser pulses for the lighting the interventional instrument responsive to reception of the trigger signals;
a first connector coupled to the laser light source that connects the laser light source to the ultrasound machine;
a micro-switch coupled to the laser light source; and
a control circuit comprising:
  a switch detect circuit to the micro-switch that is configured to:
    generate a switch signal that represents a state of the micro-switch indicating whether or not an optical connector is connected to the laser light source;
    transmit the switch signal through the first connector to the ultrasound machine;
  a blanking circuit coupled to the laser light source that is configured to:
    receive a first trigger signal from the ultrasound machine through the first connector when the state indicates that the optical connector is connected to the laser light source; and
    control generation of the laser pulses from the laser light source by preventing the reception of the trigger signals other than the first trigger signal through the first connector for a period of time after receiving the first trigger signal; and
  a memory coupled to the switch detect circuit, wherein an output of the switch detect circuit is applied to set a first address to access the memory when the state indicates that the optical connector is connected to the laser light source and to set a second address to access the memory when the state indicates that the optical connector is not connected to the laser light source.

16. The system for lighting the interventional instrument of claim 15, wherein the ultrasound machine does not generate the first trigger signal when the state indicates that the optical connector is not connected to the laser light source.

17. The system for lighting the interventional instrument of claim 15, wherein the control circuit is implemented to halt generation of laser pulses, when the optical connector is removed from the laser light source.

18. The system for lighting the interventional instrument of claim 15, wherein the first connector is an electrical connector that connects the laser light source to the ultrasound machine via a plurality of lines.

19. The system for lighting the interventional instrument of claim 15, wherein the control circuit is implemented to send a device identification (ID) identifying the laser light source to the ultrasound machine through the first connector.

20. The system for lighting the interventional instrument of claim 15, wherein sending the trigger signals are synchronized with transmitting ultrasound signals having a minimal energy by the ultrasound machine.

* * * * *